United States Patent
Lee et al.

(10) Patent No.: US 11,638,575 B2
(45) Date of Patent: May 2, 2023

(54) ULTRASONIC THERAPY AND DIAGNOSIS APPARATUS IMPLEMENTING MULTIPLE FUNCTIONS USING DETACHABLE CIRCUIT BOARDS

(71) Applicant: KOREA INSTITUTE OF SCIENCE AND TECHNOLOGY, Seoul (KR)

(72) Inventors: Byung Chui Lee, Seoul (KR); Hyung Min Kim, Seoul (KR); Ki Joo Pahk, Seoul (KR); Hyunsu Lee, Seoul (KR); Nakwon Choi, Seoul (KR); Hong Nam Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/789,881

(22) Filed: Feb. 13, 2020

(65) Prior Publication Data

US 2021/0169456 A1 Jun. 10, 2021

(30) Foreign Application Priority Data

Dec. 10, 2019 (KR) .......................... 10-2019-0163699

(51) Int. Cl.
*A61B 8/00* (2006.01)
*A61B 8/08* (2006.01)
(Continued)

(52) U.S. Cl.
CPC .............. *A61B 8/54* (2013.01); *A61B 8/4411* (2013.01); *A61B 8/4483* (2013.01); *A61B 8/52* (2013.01);
(Continued)

(58) Field of Classification Search
CPC ........... A61B 8/54; A61B 8/52; A61B 8/4411; A61B 8/4483; A61N 7/02; A61N 2007/0052; B06B 1/0215
See application file for complete search history.

(56) References Cited

U.S. PATENT DOCUMENTS 5,023,754 A * 6/1991 Aug ..................... H05K 7/1445
361/752
5,255,682 A * 10/1993 Pawluskiewicz ........ A61B 8/00
600/447
(Continued)

FOREIGN PATENT DOCUMENTS

KR          20-0244330 Y1    10/2001
KR     10-2006-0121277 A     11/2006
(Continued)

OTHER PUBLICATIONS

DIMM. Wikipedia. Wikimedia Foundation. Sep. 21, 2017. https://en.wikipedia.org/wiki/DIMM (Year: 2017).*
(Continued)

*Primary Examiner* — Oommen Jacob
(74) *Attorney, Agent, or Firm* — Birch, Stewart, Kolasch & Birch, LLP

(57) ABSTRACT

An ultrasonic diagnosis and therapy apparatus according to an embodiment may include an ultrasound output unit including a plurality of ultrasound output elements, a circuit board that can be attached and detached through a connecting board connected to the ultrasound output unit to determine a function of the ultrasound output unit, and a control unit configured to control a setting value of each of the plurality of ultrasound output elements, wherein therapy and diagnosis functions are selectively or simultaneously implemented by changing the circuit board. With the ultrasonic diagnosis and therapy apparatus, it is possible to selectively or simultaneously implement the therapy and diagnosis
(Continued)

functions by selectively mounting different types of circuit boards that determine the type and function of ultrasound outputted from the ultrasonic transducers.

7 Claims, 9 Drawing Sheets

(51) Int. Cl.
  *B06B 1/02* (2006.01)
  *A61N 7/02* (2006.01)
  *A61N 7/00* (2006.01)
(52) U.S. Cl.
  CPC .............. *A61N 7/02* (2013.01); *B06B 1/0215* (2013.01); *A61N 2007/0052* (2013.01)

(56) References Cited

U.S. PATENT DOCUMENTS

| | | | | |
|---|---|---|---|---|
| 5,505,203 | A * | 4/1996 | Deitrich | G01S 15/899 |
| | | | | 600/459 |
| 5,882,310 | A * | 3/1999 | Marian, Jr. | G10K 11/004 |
| | | | | 600/459 |
| 6,508,763 | B1 * | 1/2003 | Urbano | G01S 7/5206 |
| | | | | 600/437 |
| 2002/0035328 | A1 * | 3/2002 | Roundhill | G01S 7/5209 |
| | | | | 600/443 |
| 2003/0092992 | A1 * | 5/2003 | Kawagishi | A61B 8/481 |
| | | | | 600/458 |
| 2003/0217600 | A1 * | 11/2003 | Collins | A61B 8/4405 |
| | | | | 73/649 |
| 2004/0030227 | A1 * | 2/2004 | Littrup | A61N 7/02 |
| | | | | 600/300 |
| 2004/0082858 | A1 | 4/2004 | Fukuda et al. | |
| 2005/0096542 | A1 * | 5/2005 | Weng | G10K 11/32 |
| | | | | 600/439 |
| 2005/0154295 | A1 * | 7/2005 | Quistgaard | A61B 8/00 |
| | | | | 600/424 |
| 2007/0239001 | A1 * | 10/2007 | Mehi | G01S 7/52095 |
| | | | | 600/437 |
| 2008/0243000 | A1 * | 10/2008 | Dufort | G01S 7/52017 |
| | | | | 600/459 |
| 2008/0249409 | A1 * | 10/2008 | Fraser | A61B 8/14 |
| | | | | 600/439 |
| 2010/0286518 | A1 * | 11/2010 | Lee | A61B 8/08 |
| | | | | 600/439 |
| 2012/0209116 | A1 * | 8/2012 | Hossack | A61B 8/481 |
| | | | | 600/439 |
| 2013/0225993 | A1 * | 8/2013 | Takahashi | A61B 8/52 |
| | | | | 600/447 |
| 2013/0253327 | A1 | 9/2013 | Ko et al. | |
| 2014/0058292 | A1 * | 2/2014 | Alford | A61N 7/00 |
| | | | | 601/2 |
| 2014/0207051 | A1 | 7/2014 | Bang et al. | |
| 2015/0011885 | A1 | 1/2015 | Yoon et al. | |
| 2016/0151042 | A1 * | 6/2016 | Han | A61B 8/4433 |
| | | | | 600/443 |
| 2019/0038253 | A1 | 2/2019 | Song et al. | |
| 2020/0022681 | A1 * | 1/2020 | Wodlinger | A61B 8/5269 |

FOREIGN PATENT DOCUMENTS

| | | |
|---|---|---|
| KR | 10-2011-0074326 A | 6/2011 |
| KR | 10-1177691 B1 | 8/2012 |
| KR | 10-1411307 B1 | 6/2014 |
| KR | 10-2014-0094956 A | 7/2014 |
| KR | 10-2015-0004490 A | 1/2015 |
| KR | 10-1533402-81 | 7/2015 |
| KR | 10-2016-0080892 A | 7/2016 |
| KR | 10-2017-0027263 A | 3/2017 |
| KR | 10-2017-0091813 A | 8/2017 |
| KR | 10-2019-0132787 A | 11/2019 |
| WO | WO 2005/065408 A2 | 7/2006 |
| WO | WO 2012/015248 A2 | 2/2012 |
| WO | WO 2014/109482 A1 | 7/2014 |
| WO | WO 2018/058248 A1 | 4/2018 |
| WO | WO 2019/135160 A2 | 7/2019 |

OTHER PUBLICATIONS

ROM cartridge. Wikipedia. Wikimedia Foundation. Jan. 9, 2018. https://en.wikipedia.org/wiki/ROM_cartridge (Year: 2018).*
Nintendo 64. Wikipedia. Wikimedia Foundation. Nov. 1, 2018. https://en.wikipedia.org/wiki/Nintendo_64 (Year: 2018).*
"Expansion card." Wikipedia, Wikimedia Foundation, Accessed Jul. 19, 2022, Modified Nov. 25, 2019, https://en.wikipedia.org/wiki/Expansion_card. (Year: 2019).*

\* cited by examiner

ULTRASONIC THERAPY AND DIAGNOSIS APPARATUS IMPLEMENTING MULTIPLE FUNCTIONS USING DETACHABLE CIRCUIT BOARDS

DESCRIPTION OF GOVERNMENT-FUNDED RESEARCH AND DEVELOPMENT

This research is conducted by Korean Institute of Science and Technology and funded by the research-based hospital support program (development of non-invasive ultrasound based neural control and muscle rehabilitation systems, project serial number: 1465029123) in Ministry of Health and Welfare, neuroscience original technology development project (development of core technology for measurement/control of blood-brain barrier damage and analysis of protein modification/aggregation in brain, project serial number: 1711081876) in the Ministry of Science and ICT, and biomedical technology development project (development of ultrasonic probes and adherable devices using semiconductor technology, project serial number: 1711093060) in the Ministry of Science and ICT.

CROSS-REFERENCE TO RELATED APPLICATION

This application claims priority to Korean Patent Application No. 10-2019-0163699, filed on Dec. 10, 2019, and all the benefits accruing therefrom under 35 U.S.C. § 119, the contents of which in its entirety are herein incorporated by reference.

BACKGROUND

1. Field

The present disclosure relates to an ultrasonic diagnosis and therapy apparatus, and more particularly, to a hybrid ultrasonic diagnosis and therapy apparatus in which different types of circuit boards that determine the type and function of ultrasound outputted from ultrasonic transducers are selectively mounted/dismounted to output high-intensity or low-intensity focused ultrasound to treat a lesion, or output ultrasound for imaging to detect a lesion.

2. Description of the Related Art

To conduct therapy that mitigates a patient's pain or stimulates neural cell in a specific human body part, a method that inserts electrodes into the patient's human body has been used, but there is a risk that the human body may be damaged by this physical invasion process.

Recently, ultrasound stimulation therapy that can stimulate an affected part without a physical invasion process is widely used. Ultrasound may be classified into High-intensity Focused Ultrasound (HIFU) and Low-intensity Focused Ultrasound (LIFU) according to the intensity, and it is known that high-intensity focused ultrasound is used for direct treatment, for example, necrosis of human body tissues such as cancer cells, tumors and lesions, while low-intensity focused ultrasound can obtain medical effects without necrotizing human body tissues.

The unit of ultrasound intensity is indicated by spatial-peak temporal-average intensity (Ispta) and spatial-peak pulse average intensity (Isppa) according to the Acoustic Output Measurement Standard for Diagnostic Ultrasound Equipment by American Institute for Ultrasound in Medicine and National Electronics Manufacturers Administration (NEMA).

The standard for the type of ultrasound is not yet explicitly defined, but in general, according to U.S. FDA standards and European Safety standards, "low intensity ultrasound" is ultrasound having the spatial-peak temporal-average intensity (Ispta) of less than 3 $W/cm^2$ and refers to ultrasound within a range in which the human body is not damaged, and ultrasound having the spatial-peak temporal-average intensity of 3 $W/cm^2$ or above may be classified as "high intensity ultrasound".

Recently, medical technology is used, which treats neurological disorders such as cognitive impairment, anxiety and depression in a non-invasive way by use of low-intensity focused ultrasound (LIFU), or removes lesions in a non-invasive way by use of high-intensity focused ultrasound (HIFU).

However, it cannot identify the location of a lesion, for example, a brain tumor in real time and immediately remove the lesion, so accuracy of surgery is low, and it is impossible to accurately identify the boundaries between the lesion and other tissues, and thus there is a risk of damage of functionally important tissues that do not need to incise.

In this circumstance, as disclosed by Korean Patent Publication No. 10-2011-0074326 or WO2012/015248, studies have been made on a hybrid ultrasonic therapy apparatus including both an imaging ultrasound output device and a focused ultrasound output device to simultaneously perform diagnosis and therapy.

However, the existing ultrasonic transducer has a technical limitation that it cannot use low frequency ultrasound for therapy and high frequency ultrasound for imaging together, and thus it is necessary to use a separate ultrasonic transducer for different purposes and functions (lesion detection or lesion removal), and a difference of voltage applied to each transducer leads to a difference of life in each element. By this reason, when there is a failure in a short-lived element, it is necessary to replace other elements included in the apparatus together, causing a serious financial damage.

Additionally, a transducer array type ultrasound output device for adjusting the position of a focal point of ultrasound using a time delay of each transducer element is limited to ultrasound for imaging, and in the case of a focused ultrasound therapy apparatus having a curved surface (for example, transducers are curved themselves or a substrate is curved in the array), effective treatment is not achieved due to the fixed focal point position. To change the position of the focal point for various treatments, there is a need for a high-priced additional device to identify the position of the focal point.

SUMMARY

The present disclosure is designed to solve the above-described problems, and therefore the present disclosure is directed to providing a hybrid ultrasonic diagnosis and therapy apparatus in which different types of detachable circuit boards that determine the type and function of ultrasound outputted from ultrasonic transducers are selectively mounted to selectively or simultaneously implement therapy and diagnosis functions.

The present disclosure is further directed to providing an ultrasonic diagnosis and therapy apparatus for adjusting the position of a focal point to which ultrasound is focused as desired by setting a time delay for each of ultrasonic transducers that form an array.

Exemplary embodiments for achieving the above-described objects may be provided as below.

An ultrasonic diagnosis and therapy apparatus according to an embodiment includes an ultrasound output unit including a plurality of ultrasound output elements, a circuit board that can be attached and detached through a connecting board connected to the ultrasound output unit to determine a function of the ultrasound output unit, and a control unit configured to control a setting value of each of the plurality of ultrasound output elements, wherein a plurality of functions is selectively implemented using the circuit board.

In an embodiment, the setting value may include at least one of a frequency, a pulse repetitive frequency, a duty cycle, a time delay and an ultrasound output intensity of each of the plurality of ultrasound output elements.

In an embodiment, the control unit may be further configured to adjust position of a focal point to which the ultrasound is focused by setting the time delay of each of the plurality of ultrasound output elements.

In an embodiment, the circuit board may include a first circuit including a pulser to set the ultrasound output unit to output high-intensity focused ultrasound.

In an embodiment, the circuit board may include a second circuit including a pulser to set the ultrasound output unit to output low-intensity focused ultrasound.

In an embodiment, the circuit board may include a third circuit including a pulser and a low noise amplifier to set the ultrasound output unit to output ultrasound for imaging.

In an embodiment, the ultrasonic diagnosis and therapy apparatus may further include a processing unit to sense the ultrasound for imaging having passed through the low noise amplifier and process into an image signal.

In an embodiment, the apparatus may further include a storage unit to store different instructions corresponding to a type of the circuit board.

In an embodiment, the circuit board may include a first circuit including a pulser to allow the ultrasound output unit to output high-intensity focused ultrasound, a second circuit including a pulser to allow the ultrasound output unit to output low-intensity focused ultrasound, and a third circuit including a pulser and a low noise amplifier to allow the ultrasound output unit to output ultrasound for imaging.

According to an embodiment of the present disclosure, it is possible to selectively or simultaneously implement the therapy and diagnosis functions by selectively mounting different types of circuit boards that determine the type and function of ultrasound outputted from the ultrasonic transducers. For example, when the circuit board including the pulser is mounted, the ultrasonic transducers may operate to output focused ultrasound to remove or treat the lesion, and when the circuit board including the pulser and the low noise amplifier is mounted, the ultrasonic transducers may operate to output ultrasound for imaging to detect the lesion.

Accordingly, it is possible to selectively or simultaneously perform the ultrasonic diagnosis and/or therapy function using the ultrasonic transducers of the same specification, and it can be used in a wider range of applications than the existing ultrasonic therapy apparatus using separate transducers according to the purpose and function. Besides, since the existing ultrasonic therapy apparatus includes components such as pulsers and low noise amplifiers in one printed circuit board (PCB), when a failure occurs in an element that is prone to failure at high voltage, it is necessary to replace the entire PCB, but according to the present disclosure, when a failure occurs in the component or life expires, it is possible to reduce the repair and maintenance cost by replacing the circuit board or the transducer without needing to repair the entire apparatus.

Further, it is possible to expand the technology for changing the focal point through time delay setting of the ultrasonic transducer array that has been limited to ultrasound for imaging to focused ultrasound for therapy, so as to allow the user to adjust the position of the focal point as desired, thereby improving the convenience and economic efficiency.

DETAILED DESCRIPTION

Figure 1:
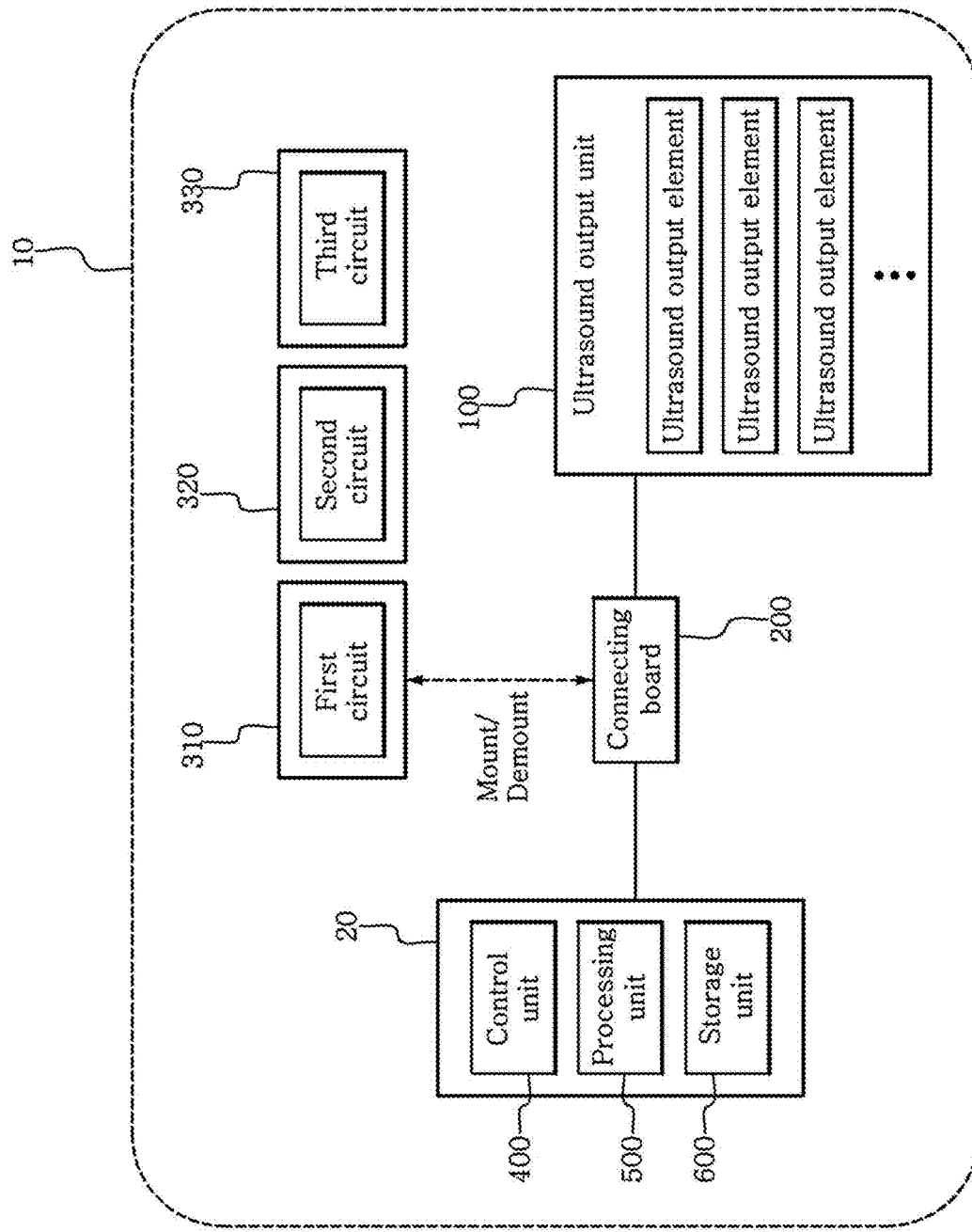
FIG. 1 is a block diagram showing the configuration of an ultrasonic diagnosis and therapy apparatus according to an embodiment of the present disclosure.

The following detailed description of the present disclosure is made with reference to the accompanying drawings, in which particular embodiments for practicing the present disclosure are shown for illustration purposes. These embodiments are described in sufficiently detail for those skilled in the art to practice the present disclosure. It should be understood that various embodiments of the present disclosure are different but do not need to be mutually exclusive. For example, particular shapes, structures and features described herein in connection with one embodiment can be embodied in other embodiment without departing from the spirit and scope of the present disclosure. It should be further understood that changes can be made to positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

Hereinafter, exemplary embodiments of the present disclosure will be described in more detail with reference to the accompanying drawings.

FIG. 1 is a block diagram showing the configuration of an ultrasonic diagnosis and therapy apparatus according to an embodiment of the present disclosure.

Referring to FIG. 1, the ultrasonic diagnosis and therapy apparatus 10 according to an embodiment includes an ultrasound output unit 100 including a plurality of ultrasound output elements, circuit boards 310 to 330 that can be attached and detached through a connecting board 200 connected to the ultrasound output unit 100 to determine the type and function of ultrasound outputted from the ultrasound output unit 100, and a body 20 connected to the connecting board 200 to control the entire apparatus.

In an embodiment, the body 20 of the ultrasonic diagnosis and therapy apparatus 10 may include a control unit 400 configured to control a setting value of each of the plurality of ultrasound output elements, a processing unit 500 to sense ultrasound for imaging having passed a low noise amplifier and process into an image signal, and a storage unit 600 to store different instructions corresponding to the types of the circuit boards. Additionally, electric circuits, control circuits and power supplies may be further included to electrically/physically couple each component and supply power or control the power supply.

Hereinafter, functions, roles and connection relationships of each component of the ultrasonic diagnosis and therapy apparatus according to an embodiment will be described in detail with reference to the accompanying drawings. The additional components such as circuits or electronic elements for supplying power to the apparatus and controlling the power supply have similar structure and principle to those of a general ultrasonic therapy apparatus in the technical field, and their detailed description is omitted herein.

The ultrasound output unit 100 includes a plurality of ultrasound output elements arranged in one- or two-dimensional array. Each ultrasound output element serves as a sound source to output ultrasound, and may include, for example, ultrasonic transducers using piezoelectric materials, CMUT, PMUT, ultrasonic transducers using the photoacoustic effect, or ultrasonic transducers using electromagnetic forces.

In general, an ultrasonic transducer converts the alternating current energy of 20 KHz or above to mechanical vibration of the same frequency using the piezoelectric effect or magnetostrictive effect. For example, the transducer includes a body with one open side and piezoelectric elements, and an electric wire is connected to each piezoelectric element to apply the voltage. The piezoelectric element uses a material exhibiting a piezoelectric effect such as quartz and tourmaline, and the transducer may generate and output ultrasound using the piezoelectric effect of the piezoelectric element. The structure of the transducer is provided for illustration purposes only, and the transducer is not limited to a particular structure or effect. The piezoelectric element of the transducer may output a proper intensity of ultrasound by adjusting the output according to the part to be treated and the purpose, and the outputted ultrasound has an overlap, forming an ultrasound beam.

Each ultrasound output element is manufactured to selectively output low-intensity focused ultrasound (LIFU), high-intensity focused ultrasound (HIFU), or high frequency ultrasound for imaging to scan lesions in human body by adjusting the frequency and output according to the part to be treated and the purpose. For example, to output high-intensity focused ultrasound, probes having attached piezo ceramic with relatively high transmission sensitivity may be used. To output low-intensity focused ultrasound or ultrasound for imaging, probes having relatively small transducers attached thereto may be used, but the type, size or material of the ultrasonic probes is not limited thereto. The therapy and diagnosis method according to the type of frequency and its effect will be described below.

Figure 2A:
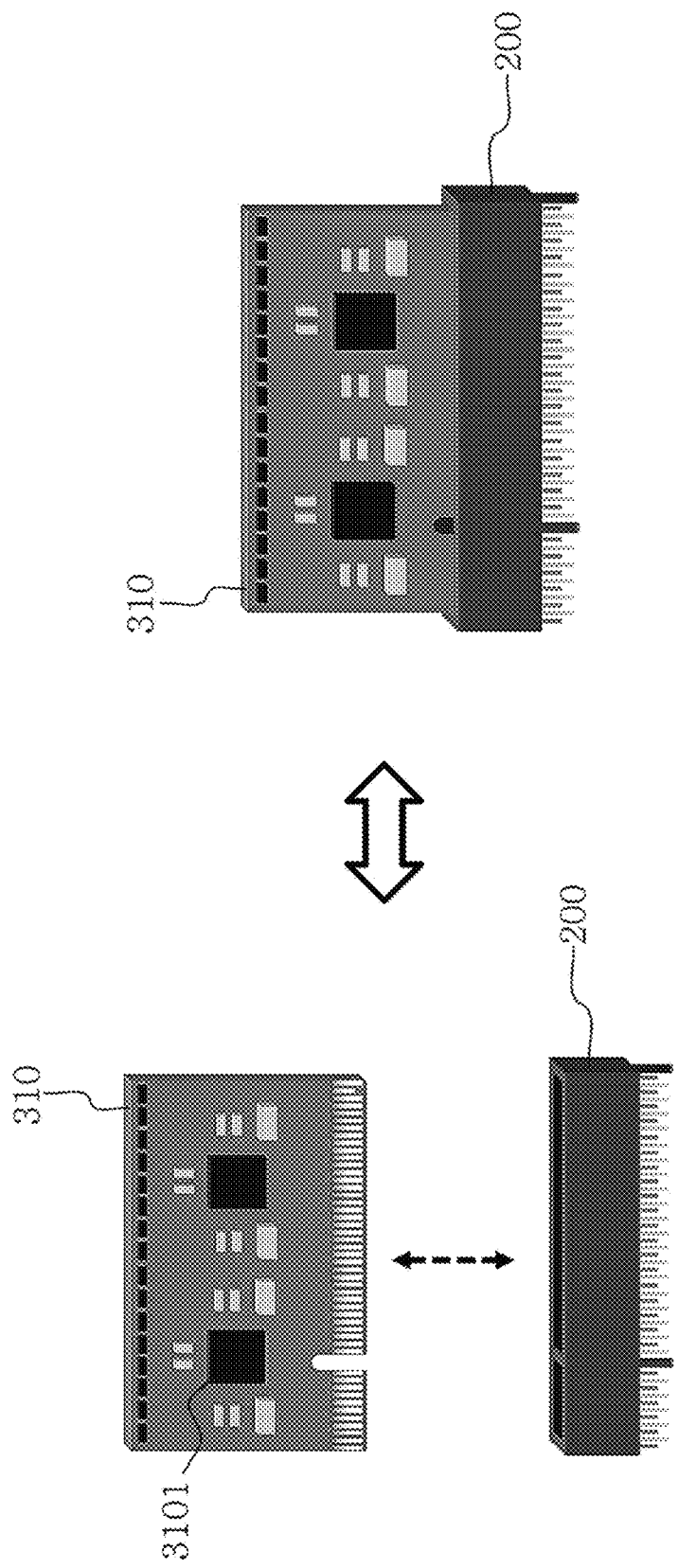
FIGS. 2A and 2B are diagrams showing attachment and detachment of a circuit board and a connecting board according to an embodiment of the present disclosure.

The connecting board 200 is a component for electrically connecting the ultrasound output unit 100 and the control unit 400 to the circuit boards 310 to 330, and has a slot for mounting/dismounting the circuit boards 310 to 330. For example, the connecting board 200 is configured to transmit and receive an input/output signal from two sides using terminals on the two sides of a substrate, such as dual in-line memory module (DIMM) board. FIG. 2A shows one circuit board 310 inserted and mounted in one connecting board 200. However, this is provided for illustration purposes only, and the connecting board 200 may have a plurality of slots to simultaneously mount a plurality of circuit boards.

Each of the circuit boards 310 to 330 includes different circuits and elements according to the type, to allow the apparatus to implement different functions, i.e., to cause different types of ultrasounds to be outputted from the ultrasound output unit, when connected to the apparatus through the connecting board 200.

In an embodiment, as shown in FIG. 1, the circuit boards 310, 320, 330 include circuits (a first circuit, a second circuit and a third circuit) to implement different functions according to their purposes.

For example, referring to FIG. 2A, the first circuit board 310 may include a first circuit including two pulsers 3101 and other elements. An ultrasonic pulser transmitter transmits an electrical signal through the circuit to allow the ultrasonic transducer to generate an ultrasonic pulse. When the first circuit board 310 is mounted in the connecting board 200 as shown in FIG. 2A, the pulser 3101 sets the ultrasound output elements to output high-intensity focused ultrasound (HIFU) through a connected channel of the ultrasound output unit 100. Although FIG. 2A shows the first circuit including two pulsers, this is provided for illustration purposes only and one or more pulsers may be included in one circuit board.

When the first circuit board 310 is mounted, the ultrasound output unit 100 outputs high-intensity focused ultrasound to treat a patient's lesion. The high-intensity focused ultrasound is used to perform treatments, for example, fat reduction, muscle rehabilitation, tissue cavitation and tumor removal by applying thermal/mechanical stimulation to the lesion. In detail, the thermal stimulation is used to burn the lesion by slowly increasing the temperature with an ultrasound beam irradiated to a corresponding focal point, and the mechanical stimulation is used to incise tissues with a high intensity continuous ultrasound beam irradiated to a corresponding focal point. However, this is an example of treatment method, but not limited thereto.

In an embodiment, in the same way as the first circuit board 310, the second circuit board 320 allows the ultrasound output unit 100 to output low-intensity focused ultrasound (LIFU) through a second circuit including one or more pulsers. The high-intensity focused ultrasound and the low-intensity focused ultrasound differ in center frequency and intensity, and this can be changed through the control unit 400, but it is possible to change the treatment method in a simple manner by changing a differently preset circuit as in the embodiment.

As opposed to the high-intensity focused ultrasound used to directly remove lesions through strong stimulation, the low-intensity focused ultrasound is used to perform treatments, for example, skin lifting, fracture treatment and chondrocyte regeneration through weak stimulation.

Figure 2B:
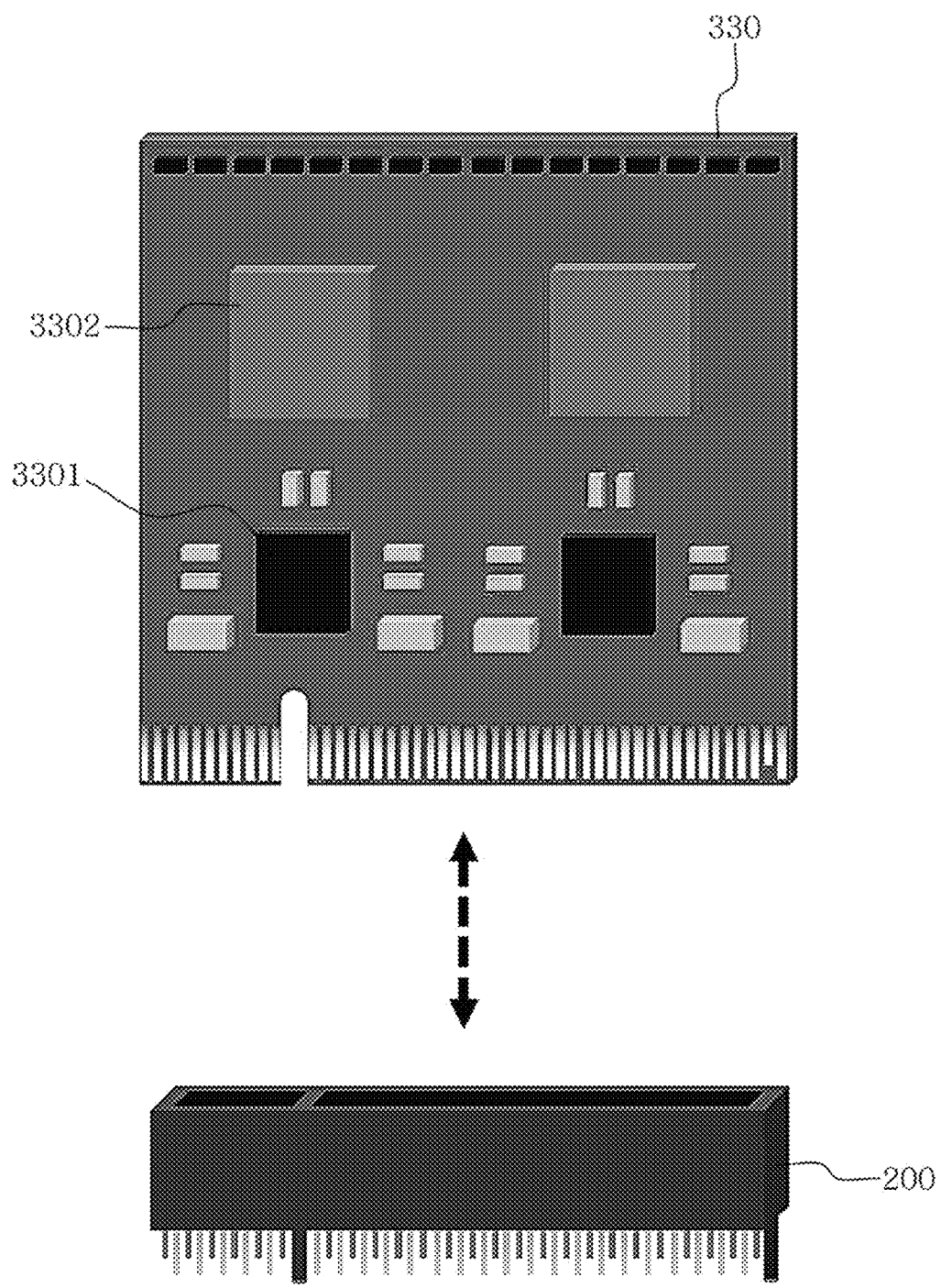

According to another embodiment, as shown in FIG. 2B, the third circuit board 330 may include a third circuit including two pulsers 3301 and two low noise amplifiers 3302. The ultrasonic pulser transmits an electrical signal through the circuit to allow the ultrasonic transducer to generate an ultrasonic pulse for imaging, and the low noise amplifier receives and amplifies the reflected ultrasound signal to fit image processing.

When the third circuit board 330 is mounted in the connecting board 200 as shown in FIG. 2B, the pulsers 3301 set the ultrasound output elements to output ultrasound for imaging through a connected channel of the ultrasound output unit 100, and the low noise amplifiers 3302 remove noise from the ultrasound signal received by a receiving unit (not shown) and amplify to fit image processing.

Likewise, although FIG. 2B shows the third circuit including two pulsers and two low noise amplifiers, this is provided for illustration purposes only and one or more pulsers and/or low noise amplifiers may be included in one circuit board.

The control unit 400 is configured to control a setting value of each of the ultrasound output elements arranged on the ultrasound output unit 100. Here, the setting value refers to an input value that can be arbitrarily set by a user, for example, a frequency, a pulse repetitive frequency, a duty cycle, a time delay, or an ultrasound output intensity as a function of peak-peak voltage of each of the ultrasound output elements.

An input unit (not shown) for inputting the setting value may include any type of input device that is easy for the user to manipulate, for example, a button, a switch, a mouse, a keyboard and a touch screen.

The setting value such as the frequency, the pulse repetitive frequency and the ultrasound output intensity may be differently set according to the treatment purpose or desired intensity of focused ultrasound for therapy, and it is possible to improve real-time detection by increasing the pulse repetitive frequency of ultrasound for imaging.

The time delay refers to a time delay between the plurality of ultrasound output elements arranged on the ultrasound output unit, and the user may adjust the position of a focal point to which ultrasound is focused by setting the time delay.

Figure 3A:
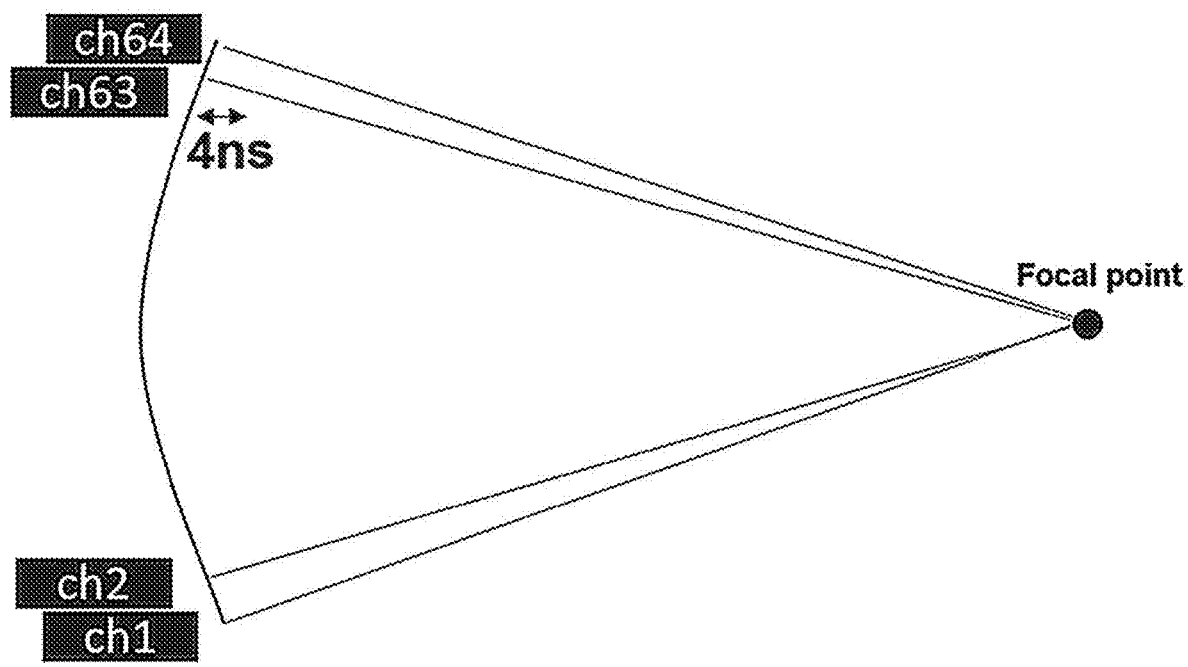
FIGS. 3A and 3B are diagrams showing adjustment of focal point position of an ultrasonic transducer array according to an embodiment of the present disclosure.
Figure 3B:
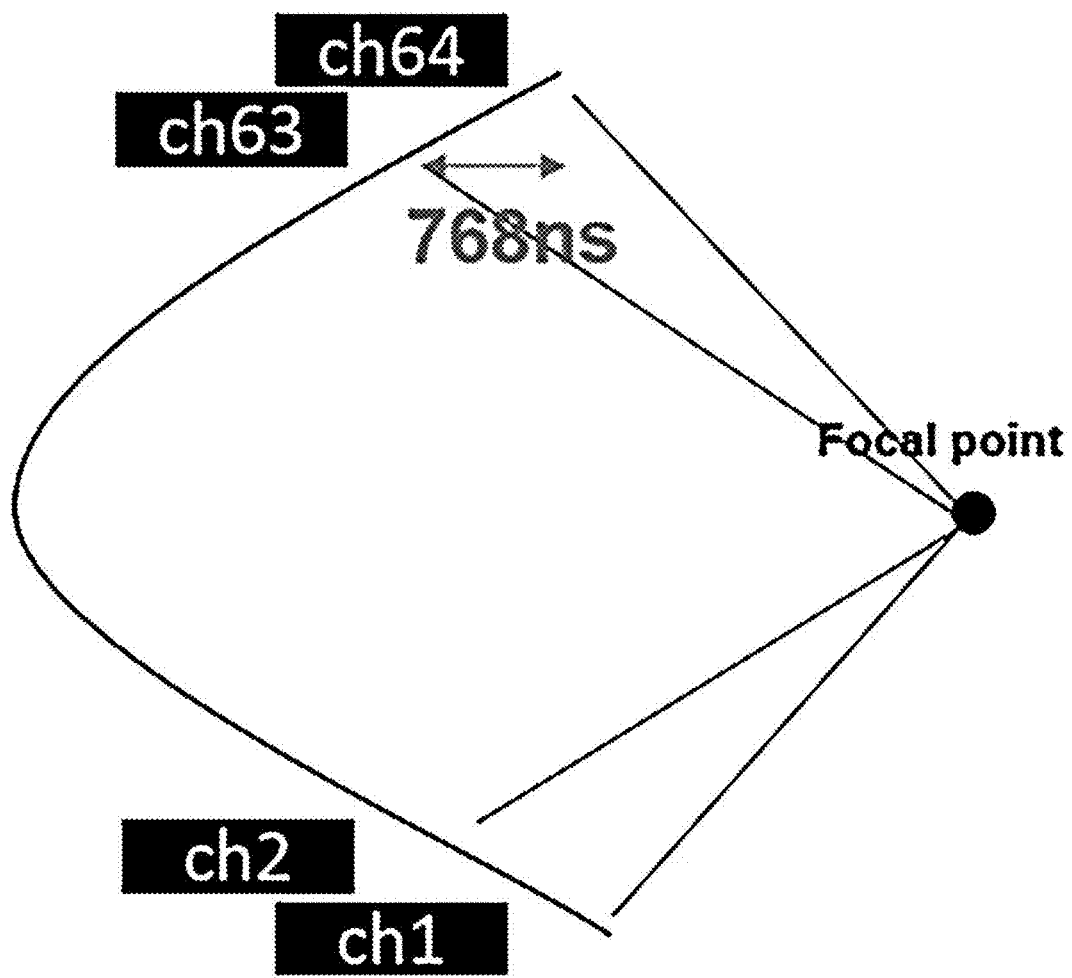

FIGS. 3A and 3B show a focal point to which ultrasound beam lines outputted from each channel are focused when the time delay value is set to 4 ns and 768 ns respectively. Here, there are 64 ultrasonic channels in total (ch1 to ch64), and this represents that the number of ultrasound output elements (transducers) included in the ultrasound output unit is 64. The ultrasound beam lines outputted from each transducer intersect at one point (focal point) where the ultrasound intensity is strongest and the treatment effect is at the maximum.

Accordingly, it is necessary to accurately focus ultrasound onto a target part to be treated, and a focal point has been formed using a plurality of ultrasonic transducers arranged on a concave substrate. However, when the fixed substrate is used to focus ultrasound, there is only one focal point, and to treat other parts, additional devices or substrates are necessary.

In this context, the present disclosure proposes technology that arbitrarily controls the position of a focal point by inputting a time delay to each transducer channel. As shown in FIGS. 3A and 3B, with the increasing time delay value, a focal point to which ultrasound beam lines are focused is formed closer to the transducers. Using this, the user can adjust the position of the focal point as desired, and there are significant improvements in convenience and economic efficiency.

In an embodiment, the ultrasonic diagnosis and therapy apparatus 10 may further include the processing unit 500 to sense ultrasound for imaging having passed through the low noise amplifier and process into an image signal. When the ultrasound for imaging is reflected by a lesion and returns to the apparatus, a sensor (not shown) senses the ultrasound, and the processing unit 500 visualizes the signal to allow the user to recognize the lesion based on a time difference. In an embodiment, the ultrasonic diagnosis and therapy apparatus 10 may further include a display unit (not shown), for example, a display, to display the processed image in real time.

The control unit 400 and the processing unit 500 may be functionally separated components within one computer processor unit, and may be each component implemented by a separate computer processor unit. A detailed description of the apparatus control and signal processing process by the computer processor unit is omitted herein.

The storage unit 600 is a component for storing different instructions corresponding to the types of the circuit boards to allow the ultrasonic diagnosis and therapy apparatus 10 to implement different functions according to the circuit boards 310 to 330. The storage unit 600 may include any type of volatile or nonvolatile memory necessary to store and execute program instructions for operating the ultrasonic diagnosis and therapy apparatus 10 according to an embodiment.

For example, to perform an ultrasonic therapy function by connecting the first circuit board or the second circuit board, among the programs stored in the storage unit 600, a program corresponding to the first circuit board 310 or the second circuit board 320 is executed to allow the ultrasound output unit 100 to output high-intensity focused ultrasound or low-intensity focused ultrasound. Alternatively, to perform an ultrasonic diagnosis function by connecting the third circuit board, among the programs stored in the storage unit 600, a program corresponding to the third circuit board 330 is executed to allow the ultrasound output unit 100 to output ultrasound for imaging. Additionally, to perform a hybrid function for simultaneous diagnosis and therapy by simultaneously connecting the first circuit board 310 and the third circuit board 330 or the second circuit board 320 and the third circuit board 330, the programs corresponding to the first circuit board 310 and the third circuit board 330 or the programs corresponding to the second circuit board 320 and the third circuit board 330, stored in the storage unit 600, are executed to allow the ultrasound output unit 100 to output high-intensity focused ultrasound from the first circuit board 310, low-intensity focused ultrasound from the second circuit board 320, and ultrasound for imaging from the third circuit board 330. The program is, for example, Verilog code, and may be uploaded onto Field Programmable Gate Array (FPGA) of the control unit 400 by the users input (or automatically).

As described above, it is possible to selectively or simultaneously implement the therapy and diagnosis functions by selectively mounting different types of circuit boards that determine the function of the ultrasonic transducers. Accordingly, when a failure occurs in the component such as the transducer or the pulser or the life expires, it is possible to reduce the repair and maintenance cost by replacing the circuit board or the transducer without needing to repair the entire apparatus.

Figure 4A:
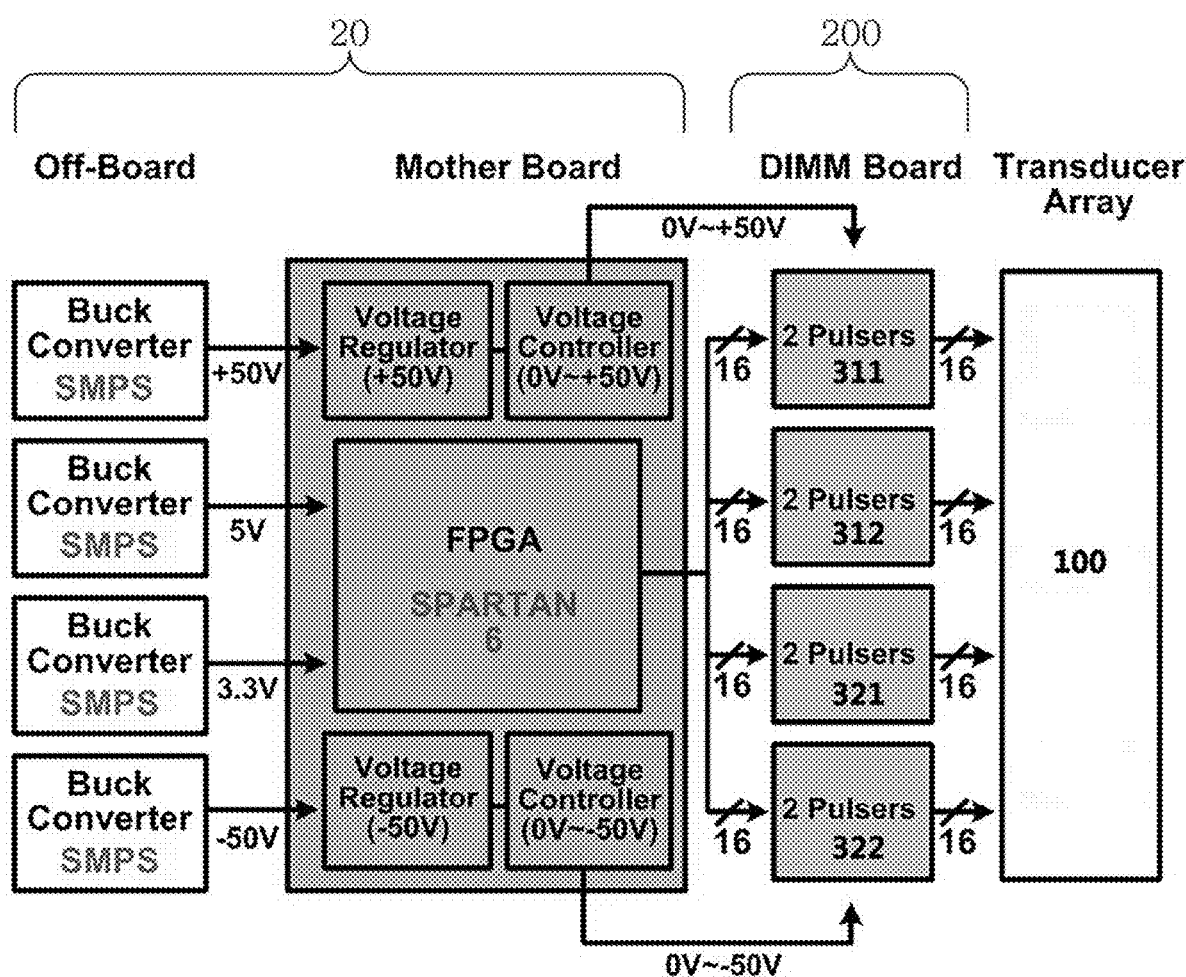
FIGS. 4A to 4C are diagrams showing the configuration and operation of an ultrasonic diagnosis and therapy apparatus according to embodiments of the present disclosure.
Figure 4B:
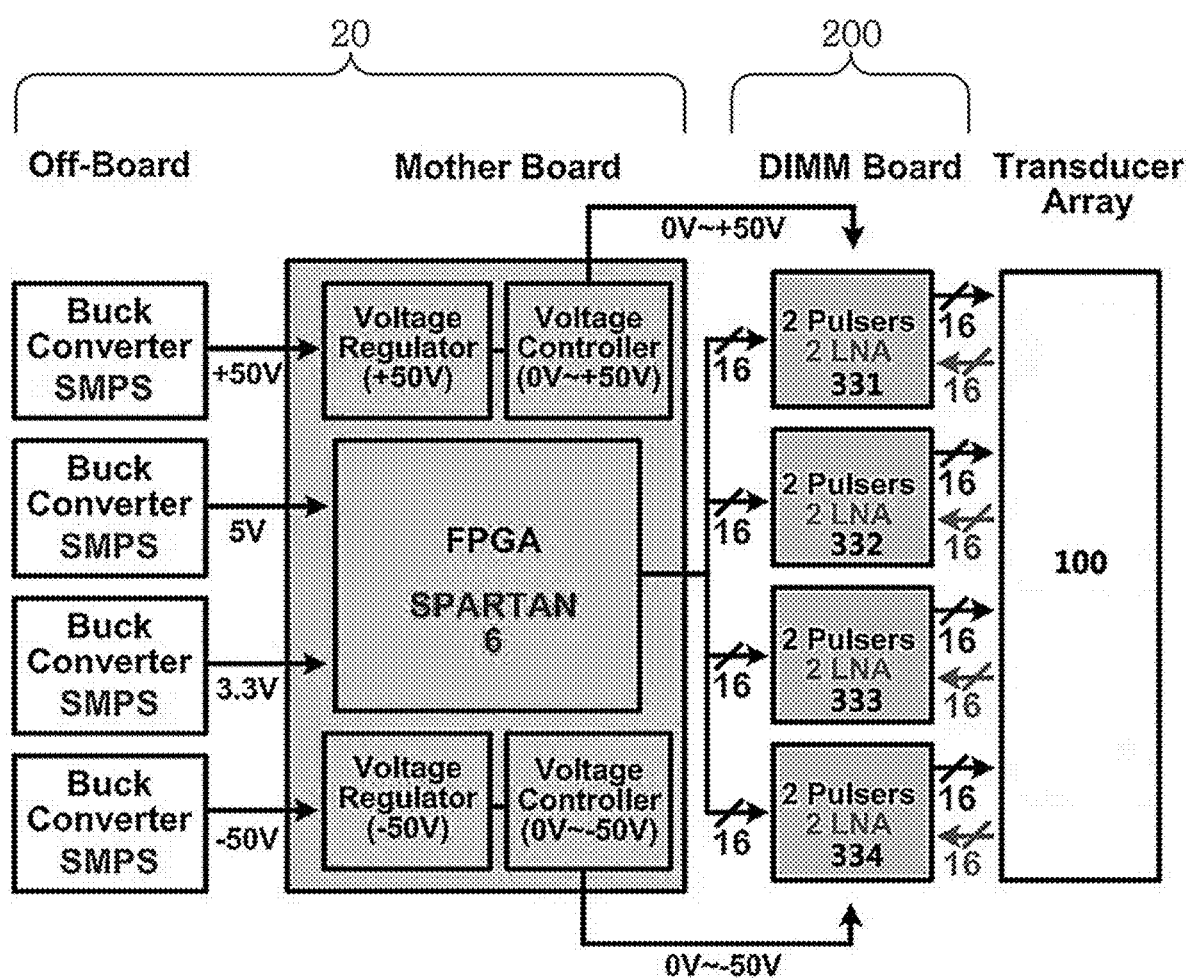
Figure 4C:
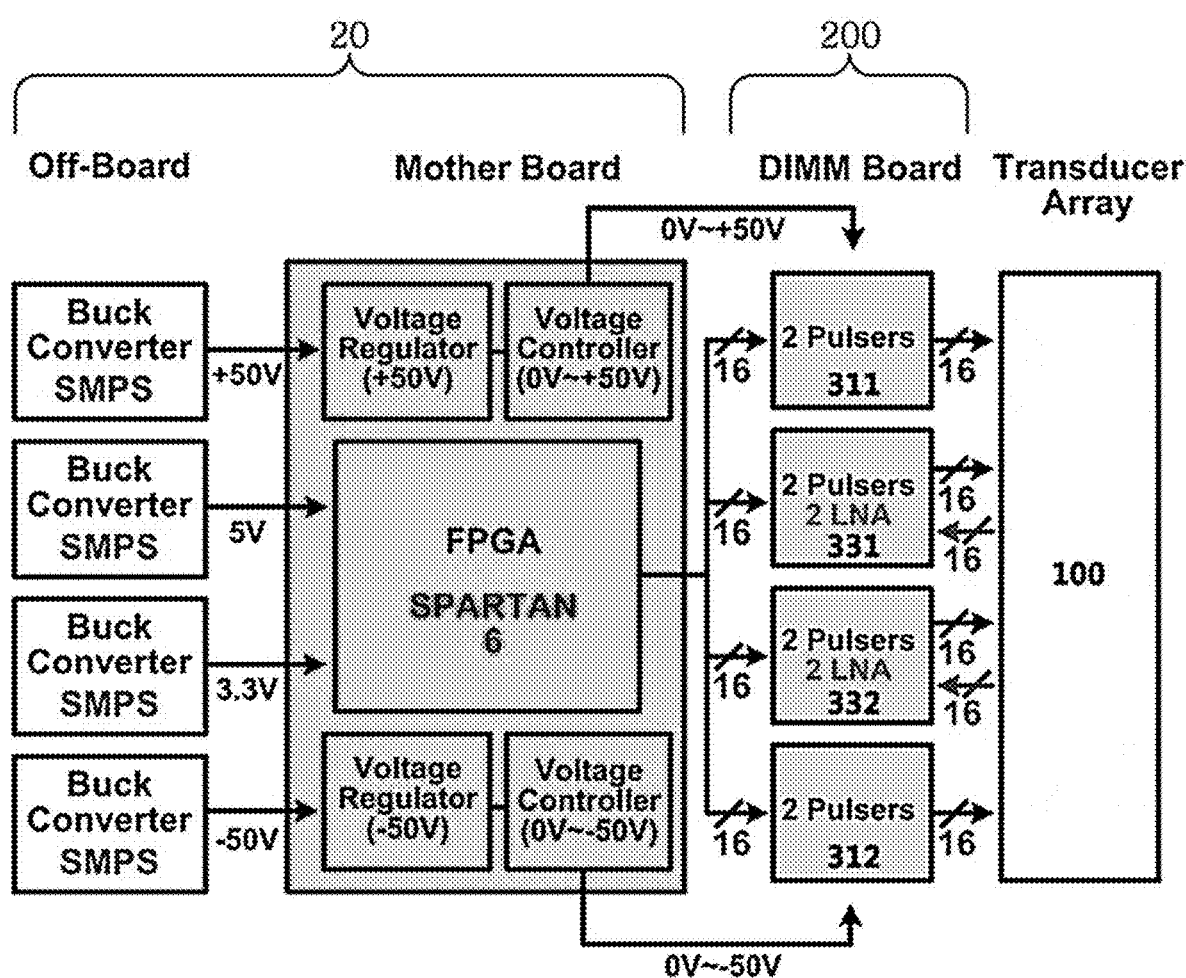

FIGS. 4A to 4C are diagrams showing the configuration and operation of the ultrasonic diagnosis and therapy apparatus according to embodiments of the present disclosure.

FIG. 4A shows the configuration of the ultrasonic diagnosis and therapy apparatus operating in 'therapy mode'. In the 'therapy mode', the ultrasonic transducer is set to output high-intensity focused ultrasound (HIFU) or low-intensity focused ultrasound (HIFU) by connecting the circuit board including the first circuit or the second circuit.

Referring to FIG. 4A, four circuit boards 311, 312, 321, 322 are mounted in the connecting board 200 having four slots. Each circuit board includes two ultrasonic pulsers. One pulser can control eight ultrasonic transducer channels, and accordingly eight (2×4) pulsers can control a total of 64 ultrasonic transducer channels. The ultrasound output unit 100 includes 64 ultrasound output elements (transducers), and each transducer outputs an ultrasound beam line so that ultrasound is focused onto one focal point. The focused ultrasound performs thermal/mechanical lesion removal (high-intensity focused ultrasound) or stimulation for skin lifting or chondrocyte regeneration (low-intensity focused ultrasound) according to the intensity. As described above, the number of pulsers included in the circuit board or the transducer channels controlled thereby are provided for illustration purposes only, but not limited by the drawings.

FIG. 4B shows the configuration of the ultrasonic diagnosis and therapy apparatus operating in 'diagnosis mode'. In the 'diagnosis mode', the ultrasonic transducers are set to output ultrasound for imaging through the ultrasound output unit 100 by connecting the circuit board including the third circuit.

Referring to FIG. 4B, four circuit boards 331, 332, 333, 334 are mounted in the connecting board 200 having four slots. Each circuit board includes two ultrasonic pulsers and two low noise amplifiers. In the same way as FIG. 4A, as one pulser controls eight ultrasonic transducer channels, eight pulsers can control a total of 64 ultrasonic transducer channels. The ultrasound for imaging outputted from the ultrasound output unit 100 is reflected by the lesion and the sensor (not shown) senses it. The sensed signal is processed by the low noise amplifier and transmitted to the processor. The processor may perform a visualization task based on the signal to allow the user to identify the lesion. Likewise, the number of pulsers included in the circuit board or the transducer channels controlled thereby are provided for illustration purposes only, but not limited by the drawings.

FIG. 4C shows the configuration of the ultrasonic diagnosis and therapy apparatus operating in 'diagnosis-therapy mode' for simultaneously performing therapy and diagnosis. In the 'diagnosis-therapy mode', one circuit board including all the first to third circuits may be connected, or a plurality of circuit boards including at least one of the first to third circuits may be connected. Accordingly, each of the ultrasonic transducer channels is set to output focused ultrasound or ultrasound for imaging.

Referring to FIG. 4C, two circuit boards 311, 312 for therapy and two circuit boards 331, 332 for diagnosis are mounted in the connecting board 200 having four slots. Each of the circuit boards 311, 312 for therapy includes two ultrasonic pulsers, and each circuit board 331, 332 for diagnosis includes two ultrasonic pulsers and two low noise amplifiers. The circuit board 311, 312 for therapy controls some (thirty two) ultrasonic transducer channels to output focused ultrasound, and the circuit boards 331, 332 for diagnosis control the remaining (thirty two) ultrasonic transducer channels to output ultrasound for imaging. Accordingly, it is possible to simultaneously perform lesion detection (diagnosis) using the ultrasound for imaging and lesion removal (therapy) using the focused ultrasound.

Although the above embodiment shows that the number of components included in the circuit board such as pulsers and low noise amplifiers is two and the transducer channels controlled by each pulser is eight, this is provided for illustration purposes only to help understanding and the number of independent elements included in the circuit and the number of channels controlled by each element are not limited thereto. For example, when the number of channels (i.e., the number of transducers) is a total of 192, 64 channels may be configured to output high frequency ultrasound for diagnosis and the remaining 128 channels may be configured to output focused ultrasound for therapy. As a larger number of channels are allocated to the output of focused ultrasound for therapy, higher intensity stimulation is achieved, and as a larger number of channels are allocated to the output of ultrasound for diagnosis, higher definition image extraction is achieved. Accordingly, it is possible to select a suitable number of channels for the purpose of treatment, and it can be used in a wider range of applications than the existing technology using a fixed number of channels.

Figure 5:
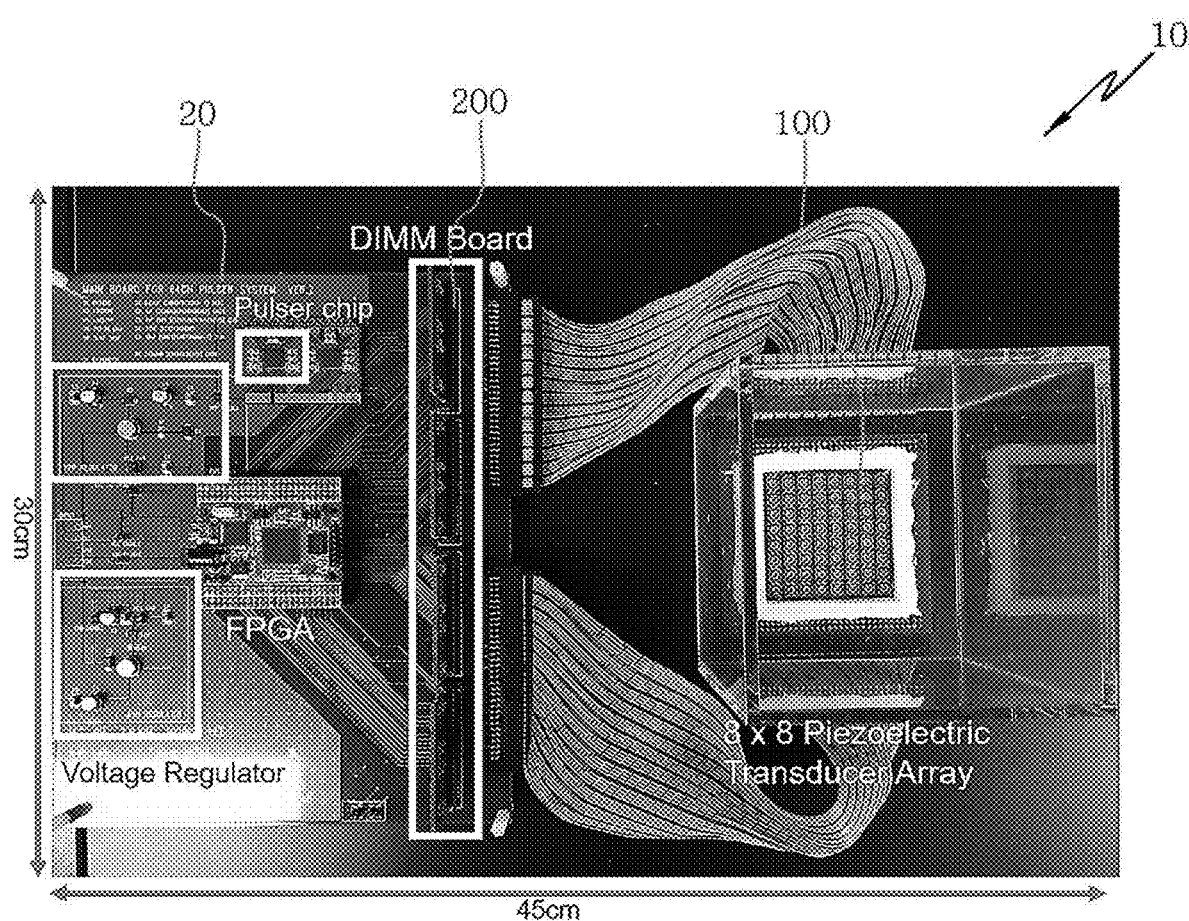
FIG. 5 shows a real configuration of an ultrasonic diagnosis and therapy apparatus according to an embodiment of the present disclosure.

FIG. 5 shows a configuration of the ultrasonic diagnosis and therapy apparatus according to an embodiment. The body 20 may include a control unit to control the components of the ultrasonic diagnosis and therapy apparatus 10, a processing unit to process an input electrical signal or a sensed ultrasound signal, and a storage unit to store program instructions for controlling and handling the components. As described above, classification of these functional blocks is represented in a simple manner to help understanding, and the real operation may be performed by one computer processor and memory, or may be performed by organic connections of multiple computer processors and memories.

The connecting board 200 of FIG. 5 includes a slot for mounting a circuit board, and when a suitable circuit board for performing a function the user desires is mounted, the corresponding program is uploaded onto the FPGA of the body 20, and the ultrasound output unit 100 outputs ultrasound for therapy and/or diagnosis according to the uploaded setting value. As shown, the ultrasound output unit 100 may include a plurality of ultrasound output elements (transducers) arranged in an array, and each transducer channel may be controlled by the inserted circuit board.

The instructions for operating the ultrasonic diagnosis and therapy apparatus according to an embodiment may be implemented as an application or in the form of program instructions that may be executed through various computer components and may be recorded in computer-readable recording media. The computer-readable recording media may include program instructions, data files and data structures, alone or in combination.

Examples of the computer-readable recording media include hardware devices specially designed to store and execute program instructions, for example, magnetic media such as hard disk, floppy disk and magnetic tape, optical media such as CD-ROM and DVD, magneto-optical media such as floptical disk, and ROM, RAM and flash memory.

Examples of the program instructions include machine code generated by a compiler as well as high-level language code that can be executed by a computer using an interpreter. The hardware device may be configured to act as one or more software modules to perform the processing according to the present disclosure, or vice versa.

Using the hybrid ultrasonic diagnosis and therapy apparatus according to the embodiments as described above, it is possible to selectively or simultaneously implement the therapy and diagnosis functions by selectively mounting different types of circuit boards that determine the function of the ultrasonic transducers. For example, when the circuit board including the pulser is mounted, the ultrasonic transducers may operate to output focused ultrasound to remove or treat the lesion, and when the circuit board including the pulser and the low noise amplifier is mounted, the ultrasonic transducers may operate to output ultrasound for imaging to detect the lesion.

Accordingly, it is possible to not only selectively or simultaneously perform the ultrasonic diagnosis and/or therapy function using the ultrasonic transducers of the same specification, but also reduce the repair and maintenance cost by replacing the circuit board or the transducer without needing to repair the entire apparatus when a failure occurs in the component such as the transducer or the pulser or the life expires.

Further, it is possible to expand the technology for changing the focal point through time delay setting of the ultrasonic transducer array that has been limited to ultrasound for imaging to focused ultrasound for therapy, so as to allow the user to adjust the position of the focal point as desired, thereby improving the convenience and economic efficiency.

While the present disclosure has been hereinabove described with reference to the embodiments, it will be understood by those having ordinary skill in the corresponding technical field that various modifications and changes may be made to the present disclosure without departing from the spirit and scope of the present disclosure as defined by the appended claims.

What is claimed is:

1. An ultrasonic apparatus, comprising:
   an ultrasound transducer including a plurality of ultrasound output elements;
   a plurality of circuit boards configured to be attachable to and detachable from a connecting board connected to the ultrasound transducer to select corresponding types and functions of ultrasound outputted from the ultrasound transducer; and
   a controller configured to control a setting value of each of the plurality of ultrasound output elements,
   wherein the connecting board is configured to electrically connect the plurality of circuit boards to the ultrasound transducer and the controller,
   wherein a plurality of types and functions of the ultrasound are selectively or simultaneously implemented using the plurality of circuit boards,
   wherein the plurality of circuit boards includes:
      a first circuit board having a first circuit including a pulser to control the ultrasound transducer to output high-intensity focused ultrasound;
      a second circuit board having a second circuit including a pulser to control the ultrasound transducer to output low-intensity focused ultrasound; and
      a third circuit board having a third circuit including a pulser and a low noise amplifier to control the ultrasound transducer to output ultrasound for imaging,
   wherein each of the plurality of ultrasound output elements is configured to selectively output the high-intensity focused ultrasound, the low-intensity focused ultrasound, or the ultrasound for imaging,
   wherein each of the plurality of circuit board configured to be separate from the ultrasound transducer and the controller is connected to the ultrasound transducer and the controller through the connecting board having a slot formed therein, and
   wherein the connecting board has a plurality of slots to simultaneously mount more than one of the plurality of circuit boards.

2. The ultrasonic apparatus according to claim 1, wherein the setting value includes at least one of a frequency, a pulse repetitive frequency, a duty cycle, a time delay and an ultrasound output intensity of each of the plurality of ultrasound output elements.

3. The ultrasonic apparatus according to claim 2, wherein the controller is configured to adjust a position of a focal point to which the ultrasound is focused by setting the time delay of each of the plurality of ultrasound output elements.

4. The ultrasonic apparatus according to claim 1, wherein the ultrasonic apparatus further comprises:
   a processor to sense the ultrasound for imaging having passed through the low noise amplifier through a sensor and process a sensed ultrasound for imaging into an image signal.

5. The ultrasonic apparatus according to claim 1, further comprising:
   a storage to store different instructions corresponding to a type of the plurality of circuit boards.

6. A non-transitory computer readable storage medium storing a computer program comprising instructions for controlling the ultrasonic apparatus to implement the plurality of types and functions of the ultrasound according to claim 1.

7. The ultrasonic apparatus according to claim 1, wherein the connecting board is configured to transmit and receive signals from two sides using terminals on the two sides of a substrate.

* * * * *